US009357904B2

(12) United States Patent
Wu

(10) Patent No.: US 9,357,904 B2
(45) Date of Patent: Jun. 7, 2016

(54) ELECTRONICALLY CONTROLLED HIGH-FREQUENCY JET VENTILATION LARYNGOSCOPE

(75) Inventor: Da Wu, Hohhot (CN)

(73) Assignee: SHANDONG YIHE MEDICAL TECHNOLOGY CO., LTD., Shandong (CN)

( * ) Notice: Subject to any disclaimer, the term of this patent is extended or adjusted under 35 U.S.C. 154(b) by 240 days.

(21) Appl. No.: 13/983,737

(22) PCT Filed: Dec. 14, 2011

(86) PCT No.: PCT/CN2011/002102
§ 371 (c)(1),
(2), (4) Date: Aug. 5, 2013

(87) PCT Pub. No.: WO2013/007001
PCT Pub. Date: Jan. 17, 2013

(65) Prior Publication Data
US 2013/0338443 A1    Dec. 19, 2013

(30) Foreign Application Priority Data
Jul. 8, 2011    (CN) .......................... 2011 1 0198119

(51) Int. Cl.
*A61B 1/267* (2006.01)
*A61B 1/015* (2006.01)
(Continued)

(52) U.S. Cl.
CPC ............. *A61B 1/015* (2013.01); *A61B 1/00066* (2013.01); *A61B 1/0676* (2013.01);
(Continued)

(58) Field of Classification Search
CPC ....... A61B 1/267; A61B 1/2676; A61B 1/015

USPC .......................................... 600/185–200, 205
See application file for complete search history.

(56) References Cited

U.S. PATENT DOCUMENTS 6,106,458 A *  8/2000  Ha .......................... A61B 1/267
                                                      600/185
2003/0182399 A1  9/2003  Silber
(Continued)

FOREIGN PATENT DOCUMENTS

CN          1164425 A      11/1997
CN          1111388 C       6/2003
(Continued)

OTHER PUBLICATIONS

International Search Report issued in International Patent Application No. PCT/CN2011/002102 dated Mar. 22, 2012.
(Continued)

*Primary Examiner* — Ellen C Hammond
*Assistant Examiner* — Christina Negrellirodrigue
(74) *Attorney, Agent, or Firm* — Oliff PLC

(57) ABSTRACT

An electronically controlled high frequency jet ventilation laryngoscope includes a laryngoscope handle and a laryngoscope blade. An oxygen supply tube is set within the laryngoscope handle and the front end of oxygen supply tube is placed on the front end of the laryngoscope blade. The laryngoscope also includes an electronic controller having a shell body, a display screen, a solenoid valve, a power supply module, a control module and a control switch. The shell body is fixed at the top of the laryngoscope handle; the display screen and control switch are on the shell body; the power supply module and control module are within the shell body; the solenoid valve is on the oxygen supply tube within the laryngoscope handle; the display screen, control module and control switch are connected with the power supply module; and the control module is connected with the display screen and the solenoid valve, respectively.

13 Claims, 7 Drawing Sheets

(51) Int. Cl.
*A61B 1/06* (2006.01)
*A61B 1/00* (2006.01)
*A61M 16/00* (2006.01)

(52) U.S. Cl.
CPC ........... *A61B 1/267* (2013.01); *A61M 16/0096* (2013.01); *A61M 16/0051* (2013.01); *A61M 2202/0208* (2013.01); *A61M 2205/502* (2013.01)

(56) References Cited

U.S. PATENT DOCUMENTS

2007/0287888 A1* 12/2007 Lovell ................ A61B 1/00094
 600/187
2011/0028790 A1* 2/2011 Farr ................... A61B 1/00052
 600/187

FOREIGN PATENT DOCUMENTS

| | | |
|---|---|---|
| CN | 200960114 Y | 10/2007 |
| CN | 101361647 A | 2/2009 |
| CN | 201365905 Y | 12/2009 |
| CN | 101647691 A | 2/2010 |
| CN | 202128786 U | 2/2012 |
| EP | 0 904 726 A1 | 3/1999 |

OTHER PUBLICATIONS

Written Opinion of the International Searching Authority issued in International Patent Application No. PCT/CN2011/002102 dated Mar. 22, 2012.

* cited by examiner

ELECTRONICALLY CONTROLLED HIGH-FREQUENCY JET VENTILATION LARYNGOSCOPE

FIELD OF TECHNOLOGY

The present invention relates to high frequency jet ventilation laryngoscopes and in particular to an electronically controlled high frequency jet ventilation laryngoscope, in the field of medical devices.

BACKGROUND OF TECHNOLOGY

Currently there are two main types of jet ventilation laryngoscope that are sold and used in the market. Both of these types of laryngoscope have different functions. A first type of laryngoscope must be used in conjunction with a high-frequency jet ventilator during the intubation process. In this process, the oxygen supply to the body is carried out with a pulse generated by the high-frequency jet ventilator through ventilation of the jet laryngoscope. The fact that this first type of laryngoscope must be used in conjunction with a high-frequency ventilator renders it inflexible, and the laryngoscope is not suitable for the trachea intubation in on-site cardiopulmonary resuscitation.

The second main type of laryngoscope is a manual jet ventilation laryngoscope. It includes a manual oxygen blocking valve disposed on the laryngoscope handle. The actuation of this valve selectively blocks the oxygen gas flow to generate a pulse, thus supplying oxygen to the body through jet ventilation. A shortcoming of this second type of laryngoscope is that the ventilation frequency needs to be manually controlled during the treatment process. Typically, the highest frequency of manual control achievable is about 30 beats-per-minute, and is insufficient to achieve the generally acceptable high-frequency ventilation frequency of 110 beats-per-minute. Moreover, in the intubation process of the trachea, it is necessary to focus on observation of the glottis, while simultaneously manually controlling the ventilation frequency. This procedure is difficult and inconvenient for the operator to perform and, even with an operator having a high degree of hand-eye coordination, the procedure is not considered an efficient patient treatment method.

SUMMARY OF THE INVENTION

To overcome the deficiencies of the above-described existing technology, it is an object of the present invention to provide an electronically controlled high-frequency jet ventilation laryngoscope.

The present invention is implemented by the following technical embodiments. In accordance with a first embodiment, there is provided an electronically controlled high-frequency jet ventilation laryngoscope which includes a laryngoscope handle and laryngoscope blade; said laryngoscope handle and said laryngoscope blade form an integral structure; an oxygen supply tube is disposed within said laryngoscope handle; the front end of said oxygen supply tube is located on the front end of said laryngoscope blade; and the lamp beads are located on the front-end of said laryngoscope blade. The laryngoscope also includes an electronic controller consisting of a shell body, a display screen, a solenoid valve, a power supply module, a control module and a control switch. Said shell body is fixed to the top of said laryngoscope handle; said display screen and control switch are located on said shell body; said power supply module and said control module are located on said shell body; said solenoid valve is located on said oxygen supply tube within said laryngoscope handle; said display screen, said control module and said control switch are connected with said power supply module; said electronic controller is selectively activated by power supplied from said power supply module; said control switch controls the opening and closing of said electronic controller; said control module is connected with said display screen and said solenoid valve, respectively; said control module controls the working frequency of said solenoid valve; and the working status of said electronic controller is displayed on said display screen.

A drug-administrating tube is disposed within said laryngoscope handle, a drug-administrating control valve is located on said drug-administrating tube; a spray orifice is located on the front end of said laryngoscope blade; and the front end of said oxygen supply tube and the front-end of said drug-administrating tube are respectively connected with said spray orifice.

Said laryngoscope handle is connected with said laryngoscope blade in a releasable snap-fit arrangement; a laryngoscope handle oxygen supply tube is disposed within said laryngoscope handle; and a laryngoscope blade oxygen supply tube is disposed within said laryngoscope blade. Said laryngoscope handle oxygen supply tube is connected with said laryngoscope blade oxygen supply tube; and said solenoid valve is located on said laryngoscope handle oxygen supply tube.

A laryngoscope handle drug-administrating tube is located on said laryngoscope handle, a drug-administrating control valve is located on said laryngoscope handle drug-administrating tube, and a laryngoscope blade drug-administrating tube is located on said laryngoscope blade. Said laryngoscope handle drug-administrating tube is connected with said laryngoscope blade drug-administrating tube; a spray orifice is located on the front end of said laryngoscope blade; the front-end of said laryngoscope blade oxygen supply tube and the front-end of said laryngoscope blade drug-administrating tube are respectively connected with said spray orifice.

Said laryngoscope blade has a hook-shaped profile, said laryngoscope blade oxygen supply tube is located on said the hook-shaped laryngoscope blade.

A laryngoscope blade drug-administrating tube is located on said hooked laryngoscope blade; a laryngoscope handle drug-administrating tube is disposed within said laryngoscope handle; and a drug-administrating control valve is located on said laryngoscope handle drug-administrating tube. Said laryngoscope handle drug-administrating tube is connected with said laryngoscope blade drug-administrating tube; said spray orifice is located on the front end of said laryngoscope blade; the front-end of said laryngoscope blade oxygen supply tube and the front-end of said laryngoscope blade drug-administrating tube are respectively connected with said spray orifice.

Said drug-administrating control valve is a drug-administrating solenoid valve; said control module is connected with said drug-administrating solenoid valve; and said control module controls the working frequency of said drug-administration solenoid valve.

Said drug-administrating control valve is a drug-administration manual control valve; and said drug-administrating manual control valve is located on the shell body of said laryngoscope handle.

The laryngoscope also includes a camera and an image processing module. Said camera is located on the front end of said laryngoscope blade and said image processing module is disposed within said shell body. Said camera is connected with said image processing module; said image processing module is connected with said display screen; the images taken by said camera are displayed on said display screen; said image processing module is connected with said control switch and said power supply module; and said camera and said image processing module are selectively activated by the power supplied by the power supply module. Said control switch controls the opening and closing of said camera and said image processing module.

The advantages of the present invention include: The oxygen supply is carried out by high-frequency jet ventilation through an electronic automatic control process during the intubation of human lung resuscitation trachea. At the same time, the cardiopulmonary resuscitation drug can be injected into the body for prompt treatment of critical patients. The self-powered laryngoscope is compact and flexible, portable, easy to operate as well as accurate and reliable to use. Thus, it is suitable to a variety of on-site resuscitation situations involving patient maneuvering.

Figure 1:
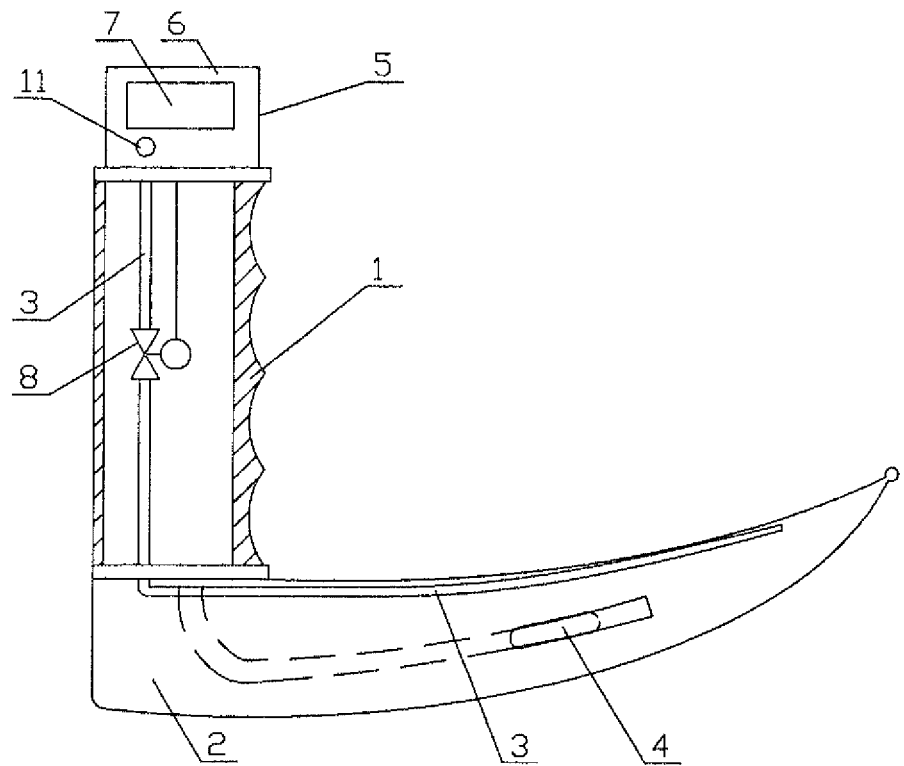
FIG. 1 is a schematic diagram of Embodiment 1.

List of features: Laryngoscope handle 1, laryngoscope blade 2, oxygen supply tube 3, lamp beads 4, electronic controller 5, shell body 6, display screen 7, solenoid valves 8, power supply module 9, control module 10, control switch 11, drug-administrating tube 12, drug-administrating control valve 13, spray orifice 14, the laryngoscope handle oxygen supply tube 15, the laryngoscope blade oxygen supply tube 16, the laryngoscope handle drug-administrating tube 17, laryngoscope blade drug-administrating tube 18, drug-administrating manual control valve 19, drug-administrating solenoid valve 20, hooked laryngoscope blade 21, camera 22, image processing module 23.

DETAILED DESCRIPTION OF THE INVENTION

Embodiment 1

Figure 2:
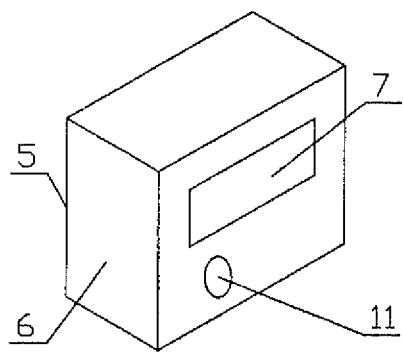
FIG. 2 is an overall schematic diagram of the electronic controller.
Figure 3:
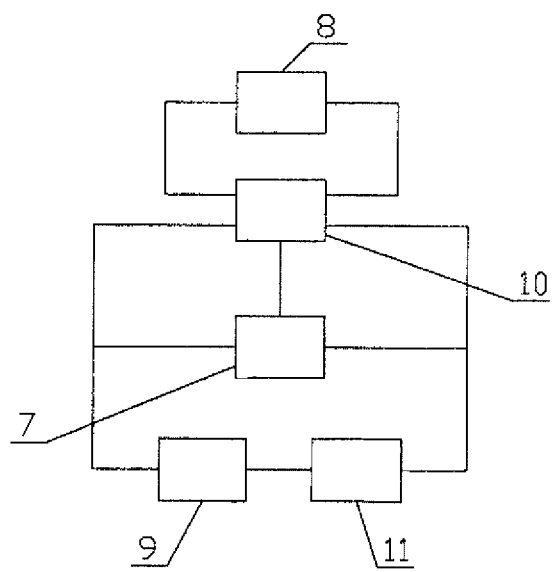
FIG. 3 is a circuit connection schematic diagram of the electronic controller.

Referring to FIGS. 1 to 3, there is shown an electronically controlled high-frequency jet ventilation laryngoscope according to a first embodiment. The laryngoscope includes a laryngoscope handle 1 and a laryngoscope blade 2. The laryngoscope handle 1 and the laryngoscope blade 2 form an integral structure. An oxygen supply tube 3 is disposed within the laryngoscope handle 1. A front-end of the oxygen supply tube 3 is placed on the front end of the laryngoscope blade 2; and lamp beads 4 are located on the front-end of the laryngoscope blade 2.

The laryngoscope also includes an electronic controller 5 which consists of a shell body 6, a display screen 7, a solenoid valve 8, a power supply module 9, a control module 10 and a control switch 11. The shell body 6 is fixed to the top of the laryngoscope handle 1. The display screen 7 and the control switch 11 are located on the shell body 6, while the power supply module 9, and the control module 10 are both disposed within the shell body 6. The solenoid valve 8 is located on the oxygen supply tube 3 within the laryngoscope handle 1. The display screen 7, control module 10 and control switch 11 are all connected with the power supply module 9. The electronic controller 5 is selectively electrically activated by power supplied from the power supply module 9. The control switch 11 controls the opening and closing of the electronic controller 5.

The control module 10, which controls the working frequency of the solenoid valve 8, is connected respectively with the display screen 7 and the solenoid valve 8. The working status of the electronic controller 5 is displayed on the display screen 7. The laryngoscope is compact and flexible, simple to operate, and the oxygen supply is carried out by high frequency jet ventilation through electronic automatic control. The amount of oxygen supplied and oxygen supply frequency are both accurately and reliably controlled. The laryngoscope is therefore suitable for a variety of on-site patient resuscitations in manoeuvring situation and can achieve the purpose to promptly treat critical patients.

Embodiment 2

Figure 4:
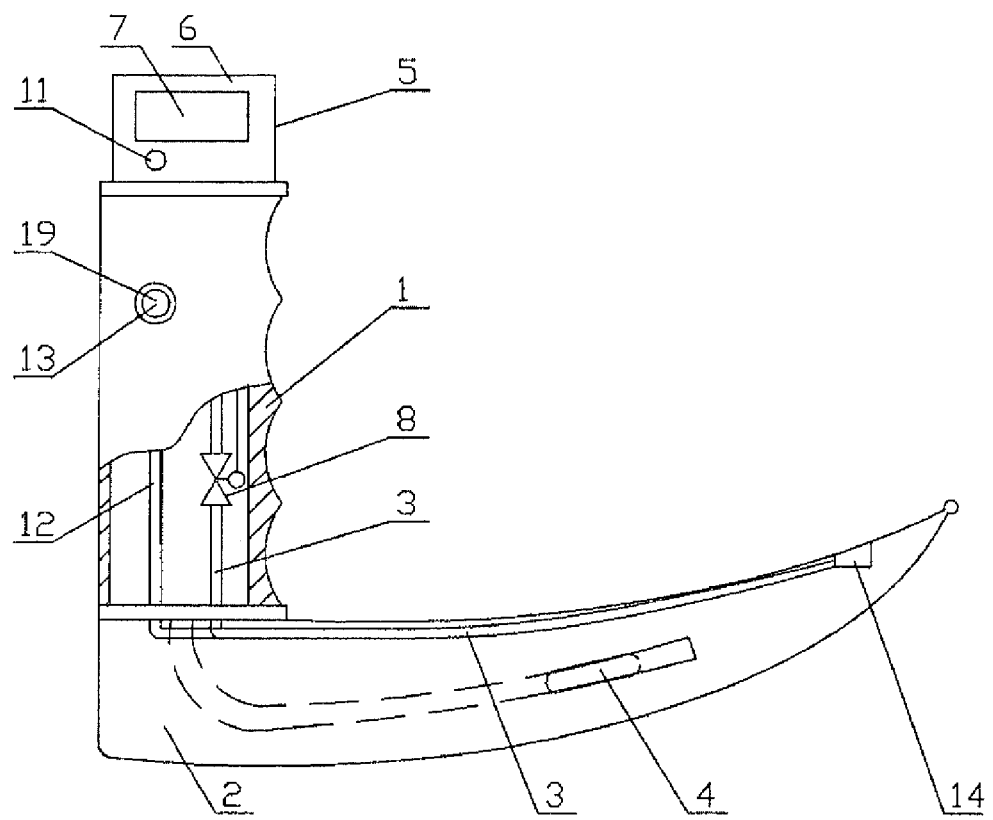
FIG. 4 is a structural schematic diagram of Embodiment 2.

Referring to FIG. 4, there is shown an electronically controlled high-frequency jet ventilation laryngoscope according to a second embodiment. The laryngoscope includes a laryngoscope handle 1, laryngoscope blade 2, oxygen supply tube 3, lamp beads 4, electronic controller 5, shell body 6, display screen 7, solenoid valve 8, power supply module 9, control module 10 and control switch 11. The position and function of these elements is the same as that described in relation to Embodiment 1 above.

The laryngoscope of Embodiment 2 also includes a drug-administrating tube 12, a drug-administrating control valve 13, a spray orifice 14, and a drug-administrating manual control valve 19. The drug-administrating tube 12 is disposed within laryngoscope handle 1, while the drug-administrating control valve 13 is disposed within the drug-administrating tube 12. The drug-administrating control valve 13 is a drug-administrating manual control valve 19 and is located on the shell of the laryngoscope handle 1.

The spray orifice 14 is located on the front-end of the laryngoscope blade 2, and the front-end of the oxygen supply tube 3 and the front-end of drug-administrating tube 12 are respectively connected with the spray orifice 14.

The laryngoscope of Embodiment 2 is compact and flexible, simple to operate, and the oxygen supply is carried out by high frequency jet ventilation through electronic automatic control. The amount of oxygen supplied and the oxygen supply frequency are both accurately and reliably controllable. When, during patient treatment, the passage of liquids is difficult to open and the cardiopulmonary resuscitation drugs cannot be injected into the body, the cardiopulmonary resuscitation drugs may be atomized and inhaled into the body through the trachea. Through this process, the speed of inhalation is faster than the intravenous injection. Thus, prompt treatment of critical patients is possible.

Embodiment 3

Figure 5:
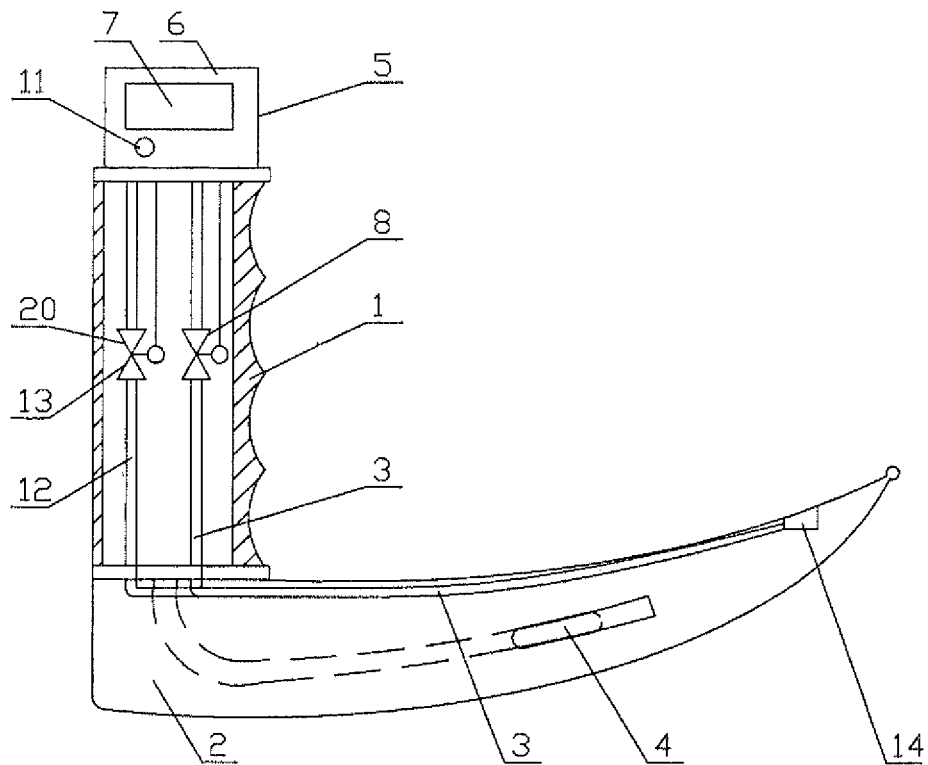
FIG. 5 is a structural schematic diagram of Embodiment 3.
Figure 6:
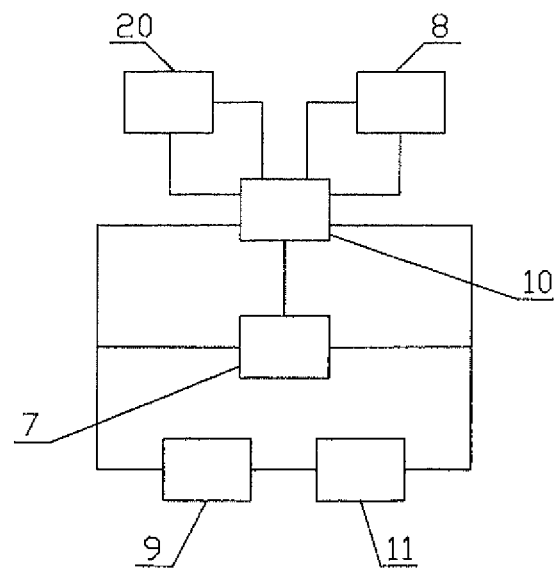
FIG. 6 is a circuit connection schematic diagram of the electronic controller in Embodiment 3.

Referring now to FIG. 5 and FIG. 6, there is shown an electronically controlled high-frequency jet ventilation laryngoscope according to a third embodiment. The laryngoscope of Embodiment 3 includes laryngoscope handle 1, laryngoscope blade 2, oxygen supply tube 3, lamp beads 4, electronic controller 5, shell body 6, display screen 7, solenoid valve 8, power supply module 9, control module 10, control switch 11, drug-administrating tube 12, drug-administrating control valve 13, spray orifice 14, and drug-administrating solenoid valve 20 common to previous embodiments. In Embodiment 3, the drug-administrating manual valve 19 in Embodiment 2 is replaced by the drug-administrating electromagnetic valve 20 and their connection structure is the same as that of the Embodiment 2. That is, the control module 10 is connected with the drug-administrating solenoid valve 20 and the control module 10 controls the working frequency of the drug-administrating solenoid valve 18.

The laryngoscope of Embodiment 3 is compact and flexible, simple to operate, and the oxygen supply is carried out by high frequency jet ventilation through electronic automatic control. The amount of oxygen supplied and the oxygen supply frequency are accurately and reliably controllable. When the passage of liquids in a patient is difficult to open and the cardiopulmonary resuscitation drugs cannot be injected into the body, the cardiopulmonary resuscitation drugs may be atomized by the electromagnetic valve 20 and inhaled into the body through the trachea. This increases the speed of inhalation over that of intravenous injection and can thus more promptly treat critical patients.

Embodiment 4

Figure 7:
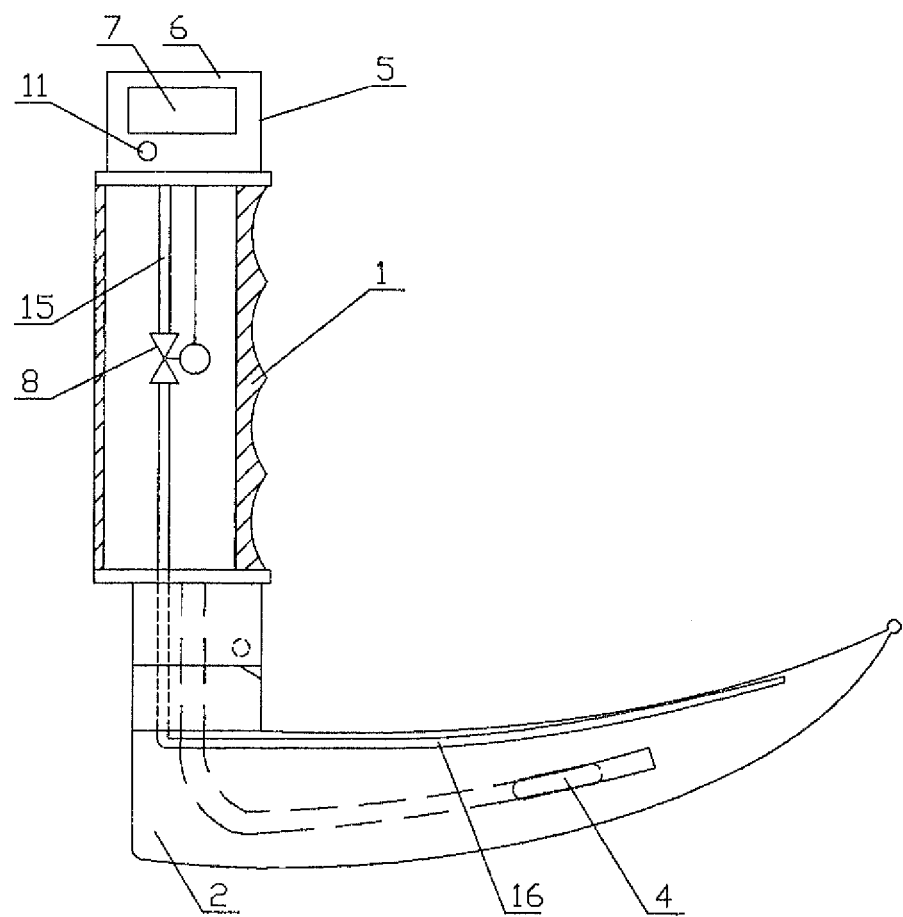
FIG. 7 is a structural schematic diagram of Embodiment 4.

Referring to FIG. 7, there is shown an electronically controlled high-frequency jet ventilation laryngoscope according to a fourth embodiment. The laryngoscope of Embodiment 4 includes a laryngoscope handle 1 and a laryngoscope blade 2, wherein the laryngoscope handle 1 is connected with the laryngoscope blade 2 in a releasable snap-fit arrangement. The laryngoscope handle oxygen supply tube 15 is disposed within said laryngoscope handle 1 and the laryngoscope blade oxygen supply tube 16 is disposed within said laryngoscope blade 2. The laryngoscope handle oxygen supply tube 15 is connected with the laryngoscope blade oxygen supply tube 16 and the lamp beads 4 are located on the front-end of the laryngoscope blade 2.

The laryngoscope also includes electronic controller 5, as per previous embodiments, which consists of shell body 6, display screen 7, solenoid valve 8, power supply module 9, control module 10 and control switch 11. The shell body 6 is fixed to the top of the laryngoscope handle 1 and the display screen 7 and control switch 11 are located on the shell body 6. The power supply module 9 and control module 10 are disposed within the shell body 6.

The electromagnetic valve 8 is located on the laryngoscope handle oxygen supply tube 15. The display screen 7, control module 10, control switch 11 are all connected with the power supply module 9. The electronic controller 5 is selectively electrically activated by power supplied from the power supply module 9 and the control switch 11 controls the opening and closing of the electronic controller 5. The control module 10 controls the working frequency of the electromagnetic valve 8 and is respectively connected with the display screen 7 and solenoid valve 8. Finally, the working status of the electronic controller 5 is displayed on the display screen 7.

The laryngoscope of embodiment 4 is simple to operate, and can use different types of laryngoscope blade 2 for patients of different ages. The oxygen supply is able to be carried out by high frequency jet ventilation through electronic automatic control. The amount of oxygen supplied and the oxygen supply frequency are both accurately and reliably controllable. When the passage of liquid is difficult to open and cardiopulmonary resuscitation drugs cannot be injected into the body, the cardiopulmonary resuscitation drugs may be atomized and inhaled into the body through the trachea. Therefore, prompt treatment of critical patients is possible with the laryngoscope of embodiment 4.

Embodiment 5

Figure 8:
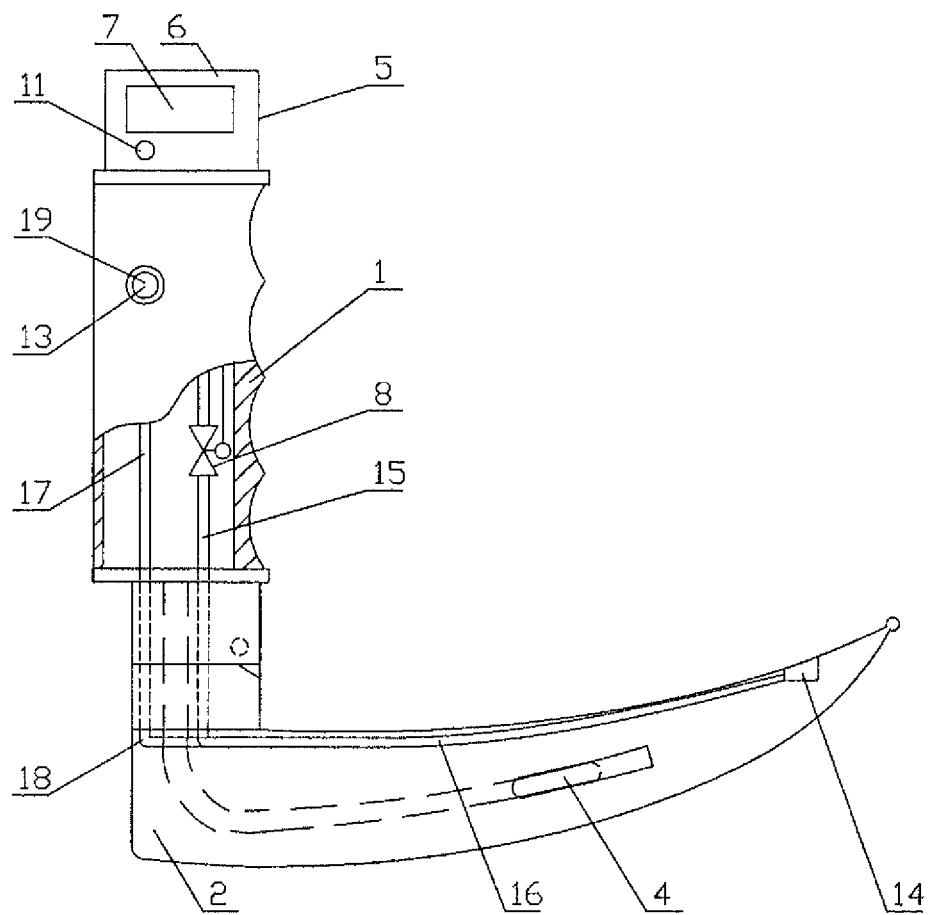
FIG. 8 is a structural schematic diagram of Embodiment 5.

Referring to FIG. 8, there is shown an electronically controlled high-frequency jet ventilation laryngoscope according to a fifth embodiment. The laryngoscope of Embodiment 5 includes a laryngoscope handle 1, laryngoscope blade 2, lamp beads 4, electronic controller 5, shell body 6, display screen 7, electromagnetic valve 8, power supply module 9, control module 10, control switch 11, laryngoscope handle oxygen supply tube 15, laryngoscope blade oxygen supply tube 16. The position and function of these elements is the same as that of Embodiment 4.

The laryngoscope also includes drug-administrating control valve 13, spray orifice 14, laryngoscope handle drug-administrating tube 17, laryngoscope blade drug-administrating tube 18, drug-administrating manual control valve 19; the laryngoscope handle drug-administrating tube 17 is set on the laryngoscope handle 1; the drug-administrating control valve 13 is set on the laryngoscope handle drug-administrating tube 17; the drug-administrating control valve 13 is a drug-administrating manual control valve 19; the drug-administrating manual control valve 19 is place on the shell body of the laryngoscope handle; the laryngoscope blade drug-administrating tube 18 is set on the laryngoscope blade 2; the laryngoscope handle drug-administrating tube 17 is connected with the laryngoscope blade drug-administrating tube 18; the spray orifice 14 is set on the front end of laryngoscope blade 2; the front-end of the laryngoscope blade oxygen supply tube 16 and the front-end of the laryngoscope blade drug-administrating tube 18 are connected with the spray orifice 14, respectively.

The laryngoscope is simple to operate, and can use different types of laryngoscope blade 2 for the patients of different ages. The oxygen supply can be carried out by high frequency jet ventilation through electronic automatic control. The oxygen supply amount and oxygen supply frequency are accurate and reliable. When the passage of liquids is difficult to open and the cardiopulmonary resuscitation drugs cannot be injected into the body, the cardiopulmonary resuscitation drugs may be atomized and inhaled into the body through the trachea and the speed of inhalation is faster than the intravenous injection, thus it can achieve the purpose to promptly treat critical patients.

Embodiment 6

Figure 9:
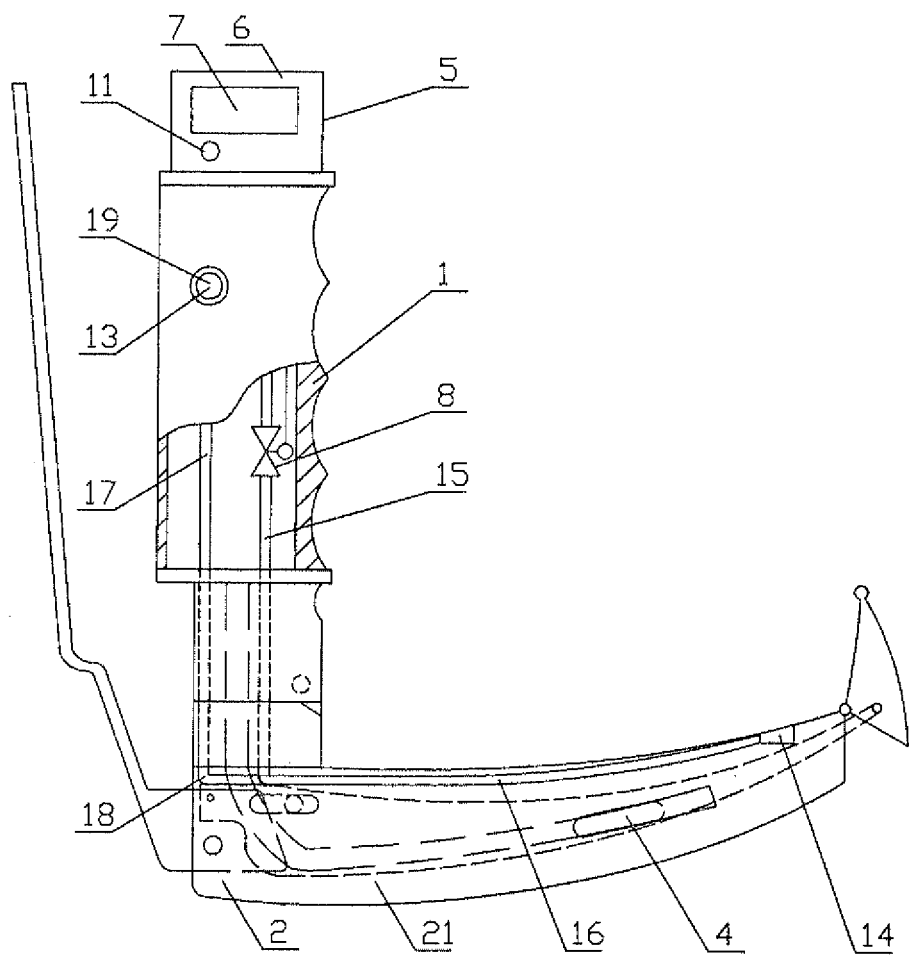
FIG. 9 is a structural schematic diagram of Embodiment 6.

Referring to FIG. 9, there is shown an electronically controlled high frequency jet ventilation laryngoscope according to a sixth embodiment. The laryngoscope of Embodiment 6 includes the laryngoscope handle 1, laryngoscope blade 2, lamp beads 4, electronic controller 5, shell body 6, display screen 7, solenoid valve 8, power supply module 9, control module 10, and control switch 11. The position and function of these elements is substantially the same as that of Embodiment 5.

The laryngoscope of embodiment 5 also includes drug-administrating control valve 13, spray orifice 14, laryngoscope handle oxygen supply tube 15, laryngoscope blade oxygen supply tube 16, laryngoscope handle drug-administrating tube 17, laryngoscope blade drug-administrating 18 and drug-administrating manual control valve 19. The laryngoscope blade 2 is in the form of hooked laryngoscope blade 21 and the laryngoscope blade oxygen supply tube 16 is location on the hooked laryngoscope blade 21. The laryngoscope blade drug-administrating tube 18 is also located on the hooked laryngoscope blade 21 and the laryngoscope handle drug-administrating tube 17 is set on the laryngoscope handle 1. The drug-administrating control valve 13 is located on the laryngoscope handle drug-administrating tube 17 and the laryngoscope handle drug-administrating tube 17 is connected with the laryngoscope blade drug-administrating tube 18. The spray orifice 14 is located on the front end of the hooked laryngoscope blade 21, and the front end of the laryngoscope blade oxygen supply tube 16 and the front end of the laryngoscope blade drug-administrating tube 18 are connected respectively with the spray orifice 14.

The laryngoscope of embodiment 6 is simple to operate, and is able to be used with different types of laryngoscope blade 2 for treating patients of different ages. The oxygen supply is able to be carried out by high frequency jet ventilation through electronic automatic control. The amount of oxygen supply and the oxygen supply frequency are both accurately and reliably controllable. In certain circumstances, a patent's throat may become obstructed and the passage of liquids is difficult to open. Sometimes in these circumstances the cardiopulmonary resuscitation drugs cannot be injected into the body and the intubation is difficult, such as high larynx, epiglottis hypertrophy and dental protrusion conditions etc. Using the laryngoscope of embodiment 6, the cardiopulmonary resuscitation drugs may be atomized and inhaled into the body through the trachea and the speed of inhalation is faster than with intravenous injection. Thus critical patients can be promptly treated.

Embodiment 7

Figure 10:
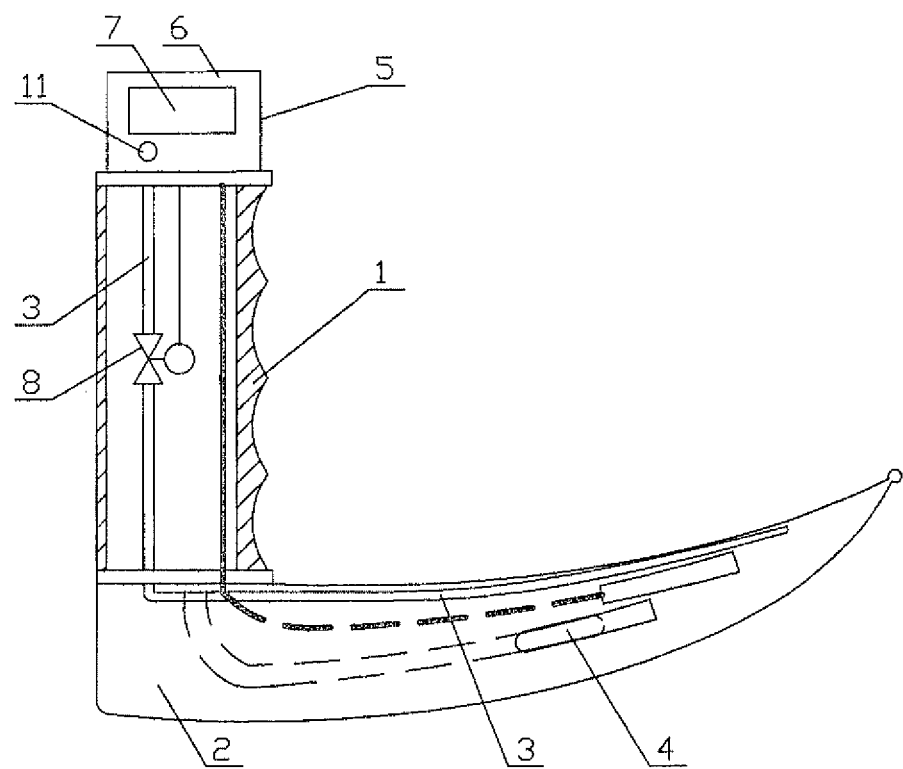
FIG. 10 is a structural schematic diagram of Embodiment 7.
Figure 11:
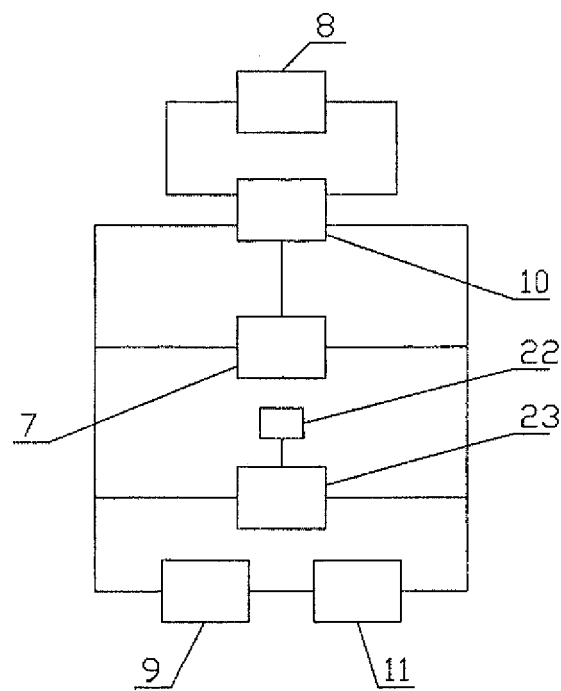
FIG. 11 is a circuit connection schematic diagram of the electronic controller in Embodiment 7.

Referring to FIG. 10 and FIG. 11, there is shown an electronically controlled high-frequency jet ventilation laryngoscope according to a seventh embodiment. The laryngoscope of embodiment 7 includes the laryngoscope handle 1, laryngoscope blade 2, oxygen tube 3, lamp beads 4, electronic controller 5, shell body 6, display screen 7, solenoid valve 8, power supply module 9, control module 10 and control switch 11 as previously described in relation to embodiment 1.

The laryngoscope of embodiment 7 also includes camera 22 and image processing module 23. The camera 22 is located on the front end of the laryngoscope blade 2 and the image processing module 23 is disposed within the shell body 6. The camera 22 is connected with the image processing module 23 and the image processing module 23 is, in turn, connected with the display screen 7. The images taken by the camera 22 are displayed on the display screen 7.

The image processing module 23 is connected with the control switch 11 and power supply module 10. The camera 22 and the image processing module 23 are selectively electrically activated by power supplied from the power supply module 9. The control switch 11 controls the opening and closing of the camera 22 and the operation of image processing module 23. In one embodiment, the image processing module 23 is an image capture card.

The laryngoscope of embodiment 7 is compact and flexible, simple to operate, and is able to be used with different types of laryngoscope blade 22 for treating patients of different ages. The oxygen supply is able to be carried out by high frequency jet ventilation through electronic automatic control. The amount of oxygen supply amount and the oxygen supply frequency are both accurately and reliably controllable. The laryngoscope of embodiment 7 is able to provide clear images for fast and accurate intubation, reduce intubation injury and cutting injury accidents. Thus, the laryngoscope of embodiment 7 is suitable to a variety of on-site resuscitation situations involving patient manoeuvring, and is able to aid in promptly treating critical patients.

What is claimed is:

1. An electronically controlled high-frequency jet ventilation laryngoscope, including:
   lamp beads;
   a laryngoscope handle having a top; and
   a laryngoscope blade having a front end, wherein
      said laryngoscope handle and said laryngoscope blade form an integral structure and an oxygen supply tube is disposed within said laryngoscope handle; and
   said oxygen supply tube includes a front end that is located on the front end of said laryngoscope blade, and the lamp beads are disposed on the front end of said laryngoscope blade;
   wherein the laryngoscope also includes an electronic controller; said electronic controller consisting of:
   a shell body;
   a solenoid valve having a working frequency;
   a power supply module;
   a control module; and
   a control switch;
   said shell body is fixed to the top of said laryngoscope handle;
   said control switch is located on said shell body;
   said power supply module and said control module are disposed within said shell body;
   said solenoid valve is located on said oxygen supply tube within said laryngoscope handle;
   said control module and said control switch are connected with said power supply module;
   said electronic controller is selectively activated by power supplied from said power supply module;
   said control switch controls opening and closing of said electronic controller;
   said control module is connected with the solenoid valve; and
   said control module controls the working frequency of said solenoid valve,
   wherein a drug-administrating tube having a front end is disposed within said laryngoscope handle; a drug-administrating control valve is disposed in said drug-administrating tube; a spray orifice is located on the front end of said laryngoscope blade, the front end of said oxygen supply tube and the front end of said drug-administrating tube are respectively connected with said spray orifice, and
   wherein said drug-administrating control valve is a drug-administrating solenoid valve having a working frequency; said control module is connected with said drug-administrating solenoid valve; said control module controls the working frequency of said drug-administrating solenoid valve.

2. An electronically controlled high-frequency jet ventilation laryngoscope according to claim 1, wherein said drug-administrating control valve is a drug-administrating manual control valve; said drug-administrating manual control valve is located on the shell body of said laryngoscope handle.

3. An electronically controlled high-frequency jet ventilation laryngoscope according to claim 1, wherein the laryngoscope also includes a camera, and an image processing module, said camera is located on the front end of said laryngoscope blade; said image processing module is disposed within said shell body; said camera is connected with said image processing module; said image processing module is connected with said display screen; the images taken by said camera are displayed on said display screen; said image processing module is connected with said control switch and said power supply module; said camera and said image processing module being selectively activated by the power supplied from said power supply module; and said control switch controls the opening and closing of said camera and said image processing module.

4. An electronically controlled high-frequency jet ventilation laryngoscope according to claim 3, wherein said electronic controller also includes a display screen set on the shell body, the control module is connected with the display screen; the display screen is connected with the power supply module; said control module controls the working frequency of said solenoid valve; and the working status of the electronic controller is displayed on said display screen.

5. An electronically controlled high-frequency jet ventilation laryngoscope according to claim 1, wherein said electronic controller also includes a display screen set on the shell body, the control module is connected with the display screen; the display screen is connected with the power supply module; said control module controls the working frequency of said solenoid valve; and the working status of the electronic controller is displayed on said display screen.

6. An electronically controlled high-frequency jet ventilation laryngoscope, including:
    lamp beads;
    a laryngoscope handle having a top; and
    a laryngoscope blade having a front end, wherein
    said laryngoscope handle and said laryngoscope blade form an integral structure and an oxygen supply tube is disposed within said laryngoscope handle; and
    said oxygen supply tube includes a front end that is located on the front end of said laryngoscope blade, and the lamp beads are disposed on the front end of said laryngoscope blade;
    wherein the laryngoscope also includes an electronic controller; said electronic controller consisting of:
    a shell body;
    a solenoid valve having a working frequency;
    a power supply module;
    a control module; and
    a control switch;
    said shell body is fixed to the top of said laryngoscope handle;
    said control switch is located on said shell body;
    said power supply module and said control module are disposed within said shell body;
    said solenoid valve is located on said oxygen supply tube within said laryngoscope handle;
    said control module and said control switch are connected with said power supply module;
    said electronic controller is selectively activated by power supplied from said power supply module;
    said control switch controls opening and closing of said electronic controller;
    said control module is connected with the solenoid valve; and
    said control module controls the working frequency of said solenoid valve,
    wherein said laryngoscope handle is connected with said laryngoscope blade in a releasable snap-fit arrangement; a laryngoscope handle oxygen supply tube is disposed within said laryngoscope handle; a laryngoscope blade oxygen supply tube is disposed within said laryngoscope blade; said laryngoscope handle oxygen supply tube is connected with said laryngoscope blade oxygen supply tube; and said solenoid valve is located on said laryngoscope handle oxygen supply tube, and
    wherein a laryngoscope handle drug-administrating tube is disposed within said laryngoscope handle; a drug-administrating control valve is located on said laryngoscope handle drug-administrating tube; a laryngoscope blade drug-administrating tube includes a front-end and is located on said laryngoscope blade; said laryngoscope handle drug-administrating tube is connected with said laryngoscope blade drug-administrating tube; a spray orifice is located on the front end of said laryngoscope blade; and the front-end of said laryngoscope blade oxygen tube and the front-end of said laryngoscope blade drug-administrating tube are respectively connected with said spray orifice.

7. An electronically controlled high-frequency jet ventilation laryngoscope according to claim 6, wherein said drug-administrating control valve is a drug-administrating solenoid valve having a working frequency; said control module is connected with said drug-administrating solenoid valve; said control module controls the working frequency of said drug-administrating solenoid valve.

8. An electronically controlled high-frequency jet ventilation laryngoscope according to claim 6, wherein said drug-administrating control valve is a drug-administrating manual control valve; said drug-administrating manual control valve is located on the shell body of said laryngoscope handle.

9. An electronically controlled high-frequency jet ventilation laryngoscope according to claim 6, wherein said electronic controller also includes a display screen set on the shell body, the control module is connected with the display screen; the display screen is connected with the power supply module; said control module controls the working frequency of said solenoid valve; and the working status of the electronic controller is displayed on said display screen.

10. An electronically controlled high-frequency jet ventilation laryngoscope, including:
    lamp beads;
    a laryngoscope handle having a top; and
    a laryngoscope blade having a front end, wherein
    said laryngoscope handle and said laryngoscope blade form an integral structure and an oxygen supply tube is disposed within said laryngoscope handle; and
    said oxygen supply tube includes a front end that is located on the front end of said laryngoscope blade, and the lamp beads are disposed on the front end of said laryngoscope blade;
    wherein the laryngoscope also includes an electronic controller; said electronic controller consisting of:
    a shell body;
    a solenoid valve having a working frequency;
    a power supply module;
    a control module; and
    a control switch;
    said shell body is fixed to the top of said laryngoscope handle;
    said control switch is located on said shell body;
    said power supply module and said control module are disposed within said shell body;
    said solenoid valve is located on said oxygen supply tube within said laryngoscope handle;
    said control module and said control switch are connected with said power supply module;
    said electronic controller is selectively activated by power supplied from said power supply module;

said control switch controls opening and closing of said electronic controller;

said control module is connected with the solenoid valve; and said control module controls the working frequency of said solenoid valve, wherein said laryngoscope handle is connected with said laryngoscope blade in a releasable snap-fit arrangement; a laryngoscope handle oxygen supply tube is disposed within said laryngoscope handle; a laryngoscope blade oxygen supply tube is disposed within said laryngoscope blade; said laryngoscope handle oxygen supply tube is connected with said laryngoscope blade oxygen supply tube; and said solenoid valve is located on said laryngoscope handle oxygen supply tube, wherein said laryngoscope blade has a hook-shaped profile, said laryngoscope blade oxygen supply tube is located on the hook-shaped laryngoscope blade, and wherein a laryngoscope blade drug-administrating tube is located on said hook-shaped laryngoscope blade; a laryngoscope handle drug-administrating tube is disposed within said laryngoscope handle; a drug-administrating control valve is located on the laryngoscope handle drug-administrating tube; said laryngoscope handle drug-administrating tube is connected with said laryngoscope blade drug-administrating tube; a spray orifice is located on the front end of said laryngoscope blade; the front-end of said laryngoscope blade oxygen supply tube and the front-end of said laryngoscope blade drug-administrating tube is connected with said spray orifice, respectively.

11. An electronically controlled high-frequency jet ventilation laryngoscope according to claim 10, wherein said drug-administrating control valve is a drug-administrating solenoid valve having a working frequency; said control module is connected with said drug-administrating solenoid valve; said control module controls the working frequency of said drug-administrating solenoid valve.

12. An electronically controlled high-frequency jet ventilation laryngoscope according to claim 10, wherein said drug-administrating control valve is a drug-administrating manual control valve; said drug-administrating manual control valve is located on the shell body of said laryngoscope handle.

13. An electronically controlled high-frequency jet ventilation laryngoscope according to claim 10, wherein said electronic controller also includes a display screen set on the shell body, the control module is connected with the display screen; the display screen is connected with the power supply module; said control module controls the working frequency of said solenoid valve; and the working status of the electronic controller is displayed on said display screen.

* * * * *